United States Patent [19]
Folsom et al.

[11] 3,938,888
[45] Feb. 17, 1976

[54] AUTOMATED PRECISION FLAME-EMISSION PHOTOMETRIC APPARATUS

[75] Inventors: Theodore R. Folsom, La Jolla; Gerald J. Parks, Jr.; William E. Weitz, Jr., both of San Diego, all of Calif.

[73] Assignee: The United States of America as represented by the Secretary of the Navy, Washington, D.C.

[22] Filed: Feb. 3, 1975

[21] Appl. No.: 546,355

[52] U.S. Cl.................................. 356/87; 356/187
[51] Int. Cl.² .......................................... G01J 3/30
[58] Field of Search ............... 356/87, 187; 431/126

[56] References Cited
UNITED STATES PATENTS
3,802,782   4/1974   Natelson .......................... 356/87 X FOREIGN PATENTS OR APPLICATIONS
145,052   4/1962   U.S.S.R................................. 356/87

OTHER PUBLICATIONS
Folsom et al., *Applied Spectroscopy*, Vol. 22, No. 2, Mar./Apr. 1968, pp. 109–114.
Folsom et al., *Applied Spectroscopy*, Vol. 24, No. 3, May/June 1970, pp. 378 and 379.

Primary Examiner—Alfred E. Smith
Assistant Examiner—F. L. Evans
Attorney, Agent, or Firm—Richard S. Sciascia; Paul N. Critchlow

[57] ABSTRACT

A net spectral intensity signal is derived from a comparison between the absolute spectral intensity of the signal interest and the intensity of a spectral continuum on which it rides. To derive the net signal, a pivotal refractor plate is mounted over the exit slit of a standard 1-meter monochromator. Pivoting of the plate produces a quick shift from the peak to its baseline signal. A programming circuit synchronizes the pivotal action with rotatably-indexed sample changer having a plural number of sample holders. The changer includes a fixed valve plate communicating with the capillary feed of a flame-emission burner and a rotatably-indexed plate having a plurality of ports each carrying a hypodermic needle for aspirating the test sample into the burner when the plate ports are mated. Repeated burnings are conducted for each sample both at the peak line and that of the spectral continuum and a multiplicity (300) of instantaneous digital signals are taken for each burning. A calculator computes an average and a standard deviation based upon the repeated burnings and upon the 300 instaneous signals.

15 Claims, 10 Drawing Figures

AUTOMATED PRECISION FLAME-EMISSION PHOTOMETRIC APPARATUS

BACKGROUND OF THE INVENTION

The invention relates to flame-emission photometric apparatus and, in particular, to precision-oriented improvements in the monochromator and in the sample changers used with such apparatus.

As is known spectrometric analysis can be achieved in a variety of ways. However, the present invention is concerned with the widely-used flame emission technique in which a liquid sample is aspirated into a flame. The resulting spectral line emission is isolated in a monochromator and passed to a phototube for producing a measurable electrical signal. This technique is considered, at least for present purposes, simpler, more effective and more precise than other techniques such, for example as the neutron activation methods used by some investigators.

I further should be recognized that the present invention has resulted primarily to permit extremely precise measurements of cesium present in the ocean or in its sediments and its organisms. Even so, as will be readily apparent, the use or applications of the present apparatus and its measurement techniques is by no means limited to the study of cesium or even to the trace amount measurements which have complicated the cesium studies.

The study of cesium and particularly the study of typical cesium concentrations in the ocean is a matter of considerable significance although, apparently, for a long time cesium has been treated as a minor alkali metal with relatively little effort directed toward its precise determination. For example, text data relating to typical cesium concentrations, over the past decades has demonstrated significant variations and it is quite clear that the data variations have been due primarily to the lack of precision in the analytical apparatus and methods. The need for advancing the art of measuring the alkali metal cesium has been recognized and described in a technical paper "Flame Photometer Specialized For Cesium" T. R. Folsom, C. Sreekumaran, W. E. Weitz, Jr., and D. A. Tennant, Applied Spectroscopy, 22 (2), March/April 1968, as well as a U.S. Patent "Flame Photometric Method and Apparatus for Quantatively Analyzing Material" Folsom, Weitz and Tennant, U.S. Pat. No. 3,588,257 issued June 28, 1971. However, even the more precise method described in these publications has proven somewhat inadequate. For example, their use has failed to disclose any statistically significant variation of cesium in the ocean even though it seems quite apparent that movement of terrestrial detritus through the ocean over a geological timescale should give rise to some differences of local concentrations of this very "rare" alkali metal.

Another matter of more practical concern is the fact that in recent years traces of the radioactive nuclides of cesium have shown up as fallout all over the world. Moreover, there now is evidence that large amounts of radioactive cesium are and will be accumulating in nuclear wastes which, accidently or otherwise, will find its way into the ocean where it will be of very real concern, particularly to marine food supplies. Manifestly, it is of considerable importance to know just how cesium traces have been distributed in the ocean over geological periods. Such analytical procedures as have been available have proven entirely too inadequate to produce reliable, realistic data.

One reason for the difficulties experienced in the measurements of cesium is the fact that this material occurs in the ocean only in very small traces mixed with much larger amounts of alkali metals. For example, the following table indicates the concentration of natural alkali metals present in sea water;

Table 1.

| Alkali | Natural alkali metals present in sea water. | |
|---|---|---|
| | Symbol | Approximate Concentration (g/) |
| cesium | Cs | 0.3 |
| rubidium | Rb | 120 |
| lithium | Li | 170 |
| potassium | K | 380,000 |
| sodium | Na | 10,500,000 |

As is obvious from the above table, any study of cesium involves the measuring of this element in microgram amounts in the presence of millions of times this amount of other elements that behave as chemicals or, at least, somewhat similarly to chemicals. Reliable measurements of these microgram amounts requires a precision and reproducibility well beyond any presently known techniques.

OBJECTS OF THE INVENTION

It is therefore an object of the present invention to produce flame-emission photometric apparatus capable of providing unusually precise and highly reproducible measurement data.

A more specific object is to provide an improved monochromator and sample changer both synchronized by a programming circuit to perform a particular procedure capable of yielding the desired precision and reliability.

Another object is to provide a special sample changer capable of performing in accordance with the other objects.

A further object is to combine the sample changer with an improved monochromator arrangement to permit the programmed operation of both with a minimum effect upon the precision of the resulting data.

Still another important object is to provide an integrating measurement technique when, when applied as a program logic to the present apparatus, produces the desired precision and reliability even when the material being tested is present in extremely small amounts.

Other objects and their attendant advantages will become more apparent in the ensuing description.

DETAILED DESCRIPTION OF THE DRAWINGS

The present invention is illustrated in the accompanying drawings of which.

DETAILED DESCRIPTION OF THE INVENTION

Figures 1, 2:
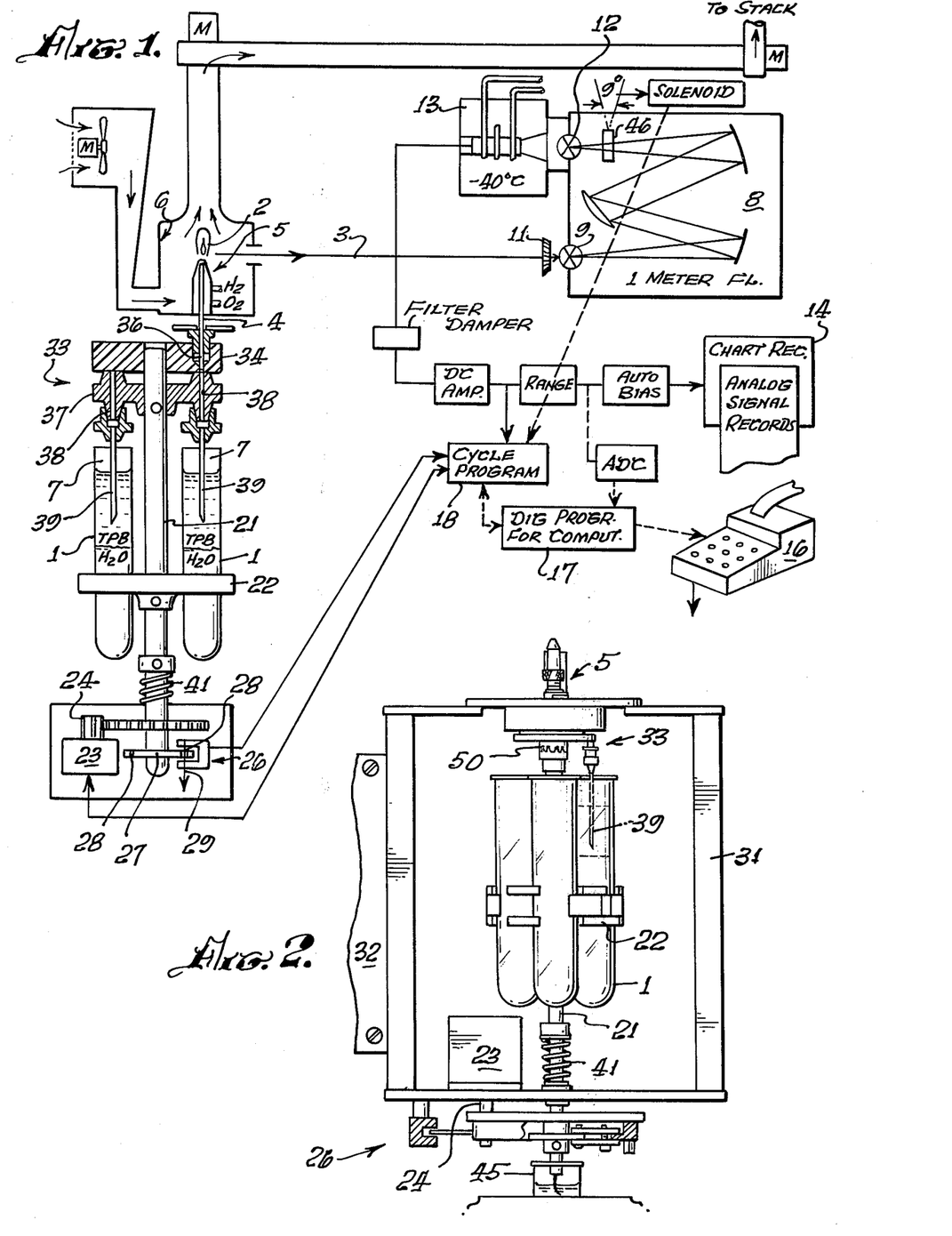
FIG. 1 is a schematic illustration of the present flame-emission spectroscopy system.
FIG. 2 illustrates a sample-changing component of the system, this figure being an assembly view of the sample changer shown in side elevation.

In the system illustrated in FIG. 1, the liquid samples to be tested are contained in a plurality of sample holders 1 from which the sample is aspirated into a flame 2 to produce spectral lines or beam 3 which then is processed and analyzed. Flame 2 is produced by a conventional burner mechanism, such as a 4020 Bechman burner, which admits hydrogen and oxygen through the identified inlets. Aspiration into the flame is accomplished in the usual manner by a conventional capillary feed tube 4. A circulatory arrangement including a hood 6 and its associated fans, conduits and motors is employed to conduct the products of combustion to an effluent stack. Obviously, this arrangement should be designed to achieve a maximum burning stability free of fluctuations and other degrading influences.

As illustrated in FIG. 1, the system is adapted primarily for determining and recording the concentration of small traces of cesium or other alkali metals present in sea water or the like. Thus, for present purposes, the liquid samples contained in holders 1 can be considered to be cesium samples. However, with very little modification, it is capable of providing superior analyses of many other liquids.

It is known that a strong optical signal at 852.1 nm can be obtained by burning small amounts, such as 0.3 micrograms of cesium dissolved in 10 ml of organic (hexonecyclohexane) solution of tetraphenylboron (TPB) in a standard total combustion aspirating burner, such as the illustrated burner 5. Obviously, the liquid samples must be very carefully prepared and a preferred procedure will be described. Also, since the analysis is concerned primarily with trace elements of the alkali metal, care must be taken to avoid losses to the walls of holders 1. Fortunately, cesium especially in acid solution, is little attracted to polyethelyne, polycarbonate or to certain other plastic surfaces so that the holders can be closed plastic cylindrical containers which, as will be noted, can be provided by ordinary test tubes. Glass, especially with basic solutions, should be avoided. This principle also is applicable to all other components with which the test sample comes into contact. Each of the test tube holders is closed by means of a plastic dust cover 7 which, as will become apparent, is functionally important.

Beam 3, which contains the optical signal of cesium at 852.1 nm is received by a standard monochromator 8 which, with one notable exception to be described, may be provided by any standard monochromator having good resolution and good stability such, for example, as a 1-meter model CT 103 of Chromatix Inc., Mountain View, Calif. In the usual manner, the monochromator is provided with an entrance slit 9 over which, preferably, is placed a bandpass interference type filter of 852.0 plus or minus 5.0. Interiorally, the beam utilized a standard lens arrangement to reflect it in a beam path ultimately focussed onto an exit slit 12 leading into a photomultiplier tube 13 which converts the optical signal into an electrical signal of commensurate strength. Exit slit 12 may include a well-known grating or equivalent device for isolating or selecting the spectral line to be processed by the phototube. As is well known in the optical arts, the selection or isolation is dependent, among other things, upon the direction of the optical beam as it impinges on or strikes the exit slit.

Phototube 13 also is a standard commercial component, operated at a low constant temperature by means of refrigeration at −40°C. The analog electrical signal produced by the tube is processed in a manner to be described and applied to a chart recorder 14 as well as a computer 16 which may be a simple desk-top calculator such as the Wang 600 model. More sophisticated implementations could utilize a control computer system or any other arrangement capable of computing and providing the desired read-out. Calculator 16 is controlled by digital program contained in block 17. In a comparable manner a cycle program of block 18 synchronizes and controls other functions of both the monochromator and the sample holder. These programming functions will be described in some detail with reference to FIG. 9.

A principle concern of the present system is to achieve unusual sensitivity and precision in the measurements of very small amounts of cesium or other alkali metals. Extremely high precision requires the suppressing of all backgrounds and signal fluctuations whenever possible and it is assumed that such measures will be applied preparatory to making the precise measurements with the flame. However, it is not widely recognized that extremely high precision can be obtained in spite of certain fluctuations that are quite difficult to express. The present system achieves this result by exploiting simple modern digital systems to progam numerous sampling and data handling operations. More specifically, the present system contemplates an automatic comparison of a plural number of unknown samples and sample standards by successively aspirating each of these samples into flame 2. Each unknown sample is rapidly compared with a standard sample and the comparisons are repeated a number of times, i.e., six or more with the comparisons being under the control of the digital programming system. The simple desk-top digital calculator, such as calculator 16, then is used to compute concentrations, means and standard deviations, all of which, as will be recognized, represent averages based upon the repeated comparisons.

Another significant burn procedure is that each sample is burned first at the peak wavelength of the material being tested, such as the peak cesium wavelength of 852.1 nm, following which the monochromator produces a wavelength shift permitting a subsequent burning at a baseline signal reference wavelength which represents the large spectral continuum on which the peak signal is riding. Generally, this comparison of peak and continuum wavelengths produces a net signal representing, for example, the cesium concentrations in the samples. Analyses based upon such net signals are quite well known. The use of optical band-pass filter 11 significantly improves the accuracy of the net signal since it effectively removes unwanted background and provides, in effect, a relatively smooth and flat continuum against which the peak wavelength is measured. Obviously, if the continuum wave form is fluctuating radically, the accuracy of the net signal measurement is reduced.

With the foregoing generalized description in mind, it now can be noted that the principle improvements in the present system reside in the sample changing mechanism which permits the plural number of sample holders to be successively rotated into communication with the flame of the burner and, additionally, in the ability to shift the wavelength quickly and simply to produce the desired net signal. Both of these mechanisms significantly contribute to the desired precision. Also, the fact that the sample changing mechanism, as well as the wavelength shifting mechanism, are under the control of a digital programming system which permits each unknown sample to be rapidly compared with a standard in a repetitive manner significantly promotes the desired sensitivity and precision. In particular, the repetitive data permits extremely precise data in spite of certain background and signal fluctuations that are quite difficult to suppress.

Before describing the apparatus, some attention should be directed toward the preparation of the cesium samples, although, as indicated, such preparatory techniques are not a direct concern of the present invention. The present system utilizes the effective and well known method of standardizing the signal by using a so-called 'spiked' solution as a yardstick. This yardstick, of course, represents a 'standard addition' which indicates the efficiency of the chemical recovery as well as the standardized brightness of the flame. In this procedure, a number of samples are prepared some of which contain the unknown solution while others include a spiked aliquot. For example, the sample changer may include four sample tubes arranged in such a manner that a spiked aliquot follows its unspiked aliquot. Thus, the unknown sample and its spiked mate provide a pair of samples which can be burned to provide single first estimate of the concentrations. A second pair may follow the first pair in sequence and additional concentration data computed. When each of these pairs is sequentially burned a plural number of times, the repetition is capable of producing precise statistical information. Of course, other sequences can be utilized to the extent that instead of burning duplicate pairs, the second pair can include a second unknown and its spiked aliquot or the system may be used to burn concentrates from samples of reference sea water without an internal standard.

In preparing cesium samples, the desired amount of cesium is extracted from 1-liter samples of sea water using a so-called Feldman and Rains procedure described in the following publications: Folsom, Feldman and Rains, Science 144, 538, (1964) and Feldman and Rains, Analytical chemistry 36, 405, (1964). In this procedure, each 1-liter of acidified sea water sample is contacted with one gram of highly purified AMP in ½ gallon, closed plastic containers which are rotated slowly at about 30 rpm around a horizontal shaft of a special gang tumbler. Each unknown aliquot then is tumbled together with a spiked aliquot and, if desired, with one or more standard reference sea water samples with or without added spikes of their own. After overnight settling, the AMP is transferred into a second plastic container for two or more extractions. The samples and standards next are handled in 100 ml propylene centrifuge tubes which are the test tubes identified as sample holders 7 of FIG. 1. Two tumbling operations are conducted with the tube being covered by plastic sheet clamped over their top portion. The first extraction within these tubes is into 100 mg of purified AMP and the AMP is centrifuged down and dissolved by adding sodium hydroxide. This solution then is contacted with exactly 10 ml of organic TPB solution during a second tumbling operation. The resulting 10 ml of concentrate standing above the aqueous phase in the centrifuge tube then is ready for burning, although identical spiked concentrates as well as any required reference sample concentrates also must be ready on the same tumbler. As shown in FIG. 1, the sample holders 1 contain the requisite amount of cesium extracted into TPB standing above an aqueous phase and the holders are closed at their tops by plastic sheets 7 which serve, among other things, as dust covers. However, although the extraction procedure produces a 100 fold concentrate, it does not remove all of the other alkalis and it is for this reason that the cesium spectral peak must be measured while riding on a large spectral continuum. In other words, the presence of the other alkalis requires the previously-described wavelength changing for each sample burn for the purpose of producing a net signal or, in other words, a signal derived by subtracting the spectral line continuum which, when applied to cesium measurements, may be a region of about 852.5 nm. As would be expected, the wavelength used as the yardstick or, in other words, the baseline wavelength is not particularly critical although the wavelength used for peak measurements is extremely critical.

As far as apparatus is concerned, the principle features of the invention, as has been stated, involve improvements in the sample changing mechanism and in the monochromator which permits the described wavelength change for each burning. The sample changing mechanism is illustrated in FIGS. 1–5. With attention directed particularly to FIGS. 1 and 2, it will noted that the sample changer includes four of the previously identified sample-holders 1 carried by a rotatable shaft 21 and an appropriate clamping mechanism 22. Preferably, the sample-holders, which are plastic test tubes, are disposed in a circular arrangement at 90° intervals and shaft 21 is sequentially rotated in 90° increments under the control of the cycle program contained in block 18 (FIG. 1).

Specifically, the cycle program controls a step motor 23 driving a geared shaft 24 which, in turn, drives circular gear 25 secured to shaft 21. Indicator mechanism 26 insures a precise indexing of the shaft in each of its rotated positions and, although this indicator may assume a variety of forms, one suitable implementation includes a disc 27 mounted on the shaft and provided with a plurality of apertures or small bore openings 28 permitting a beam 29 to pass through the disc when the shaft is indexed in its desired position. Disc 27 is driven by the shaft through a gear train designed to rotate the disc a fixed amount in each shaft rotation. Other types of indicators, of course, can be substituted providing they have the requisite accuracy. The passage of beam 29 through the aperture closes a circuit 30 to cycle program 18 to trigger the drive of the shaft. The entire sample changing mechanism is mounted in a suitable frame 31 (FIG. 2) held in a stable disposition by a plate 32.

Figures 3, 4, 5:
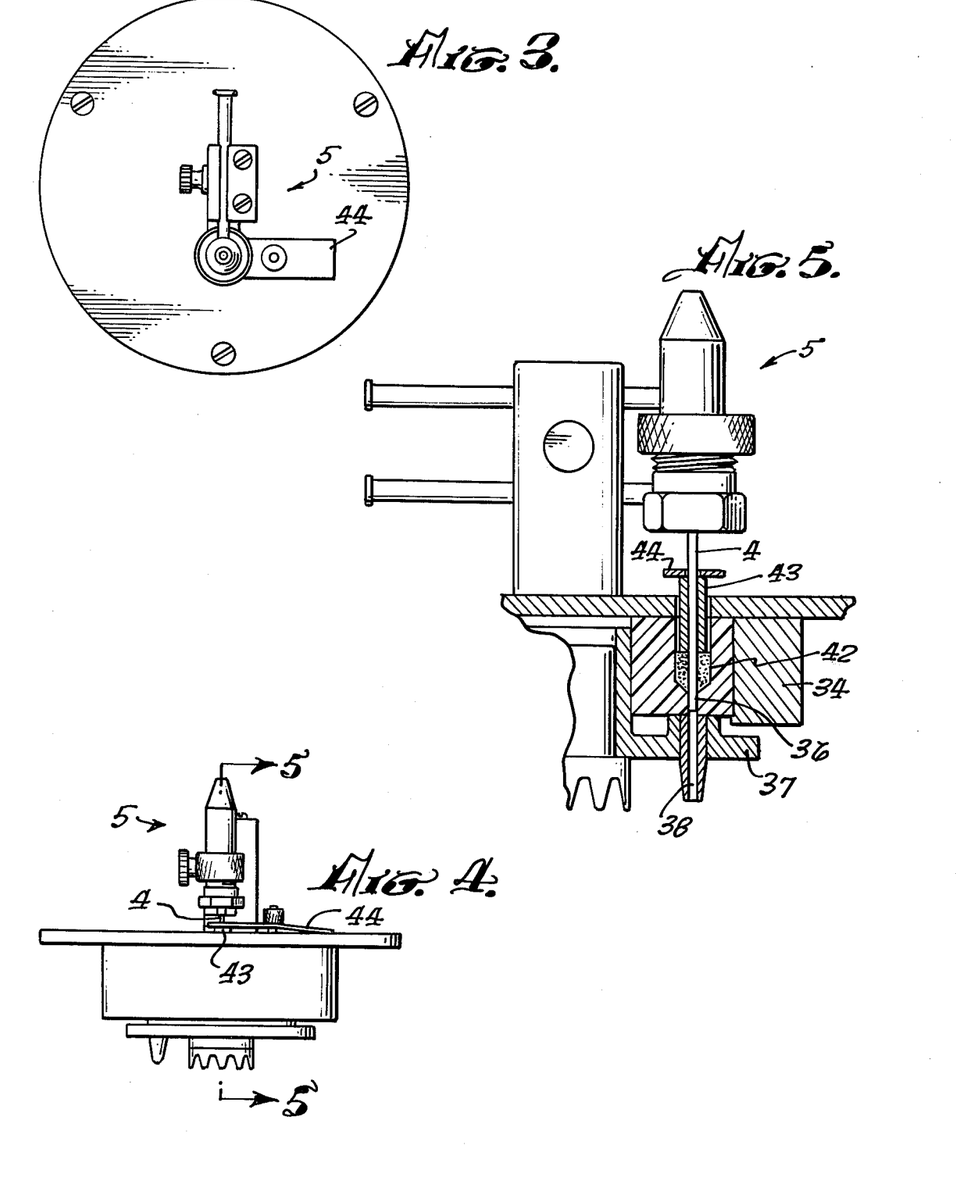
FIGS. 3 and 4 are top and side views of a special sample changer valving arrangement.
FIG. 5 is a section of the valve structure taken along lines 55 of FIG. 4.

The principle function of the sample changer is to successively communicate the liquid sample contained in each sample holder 1 with burner 5 or, more specifically, with aspirating capillary tube 4 of the burner. For this purpose, the changer includes a multiported, flat-faced valve arrangement generally identified in FIG. 1 by numeral 33. Structural details of the valve mechanism are shown in FIGS. 3, 4 and 5. Valve mechanism 33 includes a fixed plate 34 secured to frame 31 and provided with a central bore in which shaft 21 is journaled. The plate being provided with a single port 36 receiving capillary tube 4 of the burner. The second part of valve mechanism 33 is a second plate 37 carried by shaft 21 so as to be sequentially indexed in a rotary manner by the shaft. In contrast to fixed plate 34, rotatable plate 37 is provided with four ports 38 disposed circumferentially at a 90° spacing in conformity with the 90° spacing of test tube holders 1. Each of these ports, in turn, mounts a capillary tube 39, which, preferably, is a hypodermic needle sized to conform with the dimensions of bore 38 and capillary feedtube 4 of the burner. Each needle, as shown, has a pointed end which, in preparing the changer for the testing procedure is pierced through plastic dustcovers 7 of the test tubes into the contained cesium sample. Consequently, as shaft 21 is rotated in its programmed manner, each of the test tubes and the hypodermic needles is aligned through bore 38 of the rotatable plate with bore 36 of the fixed plate to communicate the sample with the flame of the burner and permit the sample to be aspirated into the flame. As previously noted, the shaft also rotates the optical indicator through approximate reduction gearing.

One of the advantages of this valve arrangement is that it permits the sequential burning of successive samples in the same flame and without admitting air to capillary tube 4 of the burner between the successive burnings. In this regard, it might be noted that conventionally self-aspirating total consumption burners employ an arrangement in which the aspirated tube is dipped into a sequence of sample cups on an automatic sample cup changer. However, this type of sample changer admits air to the aspirated tube between the sample burnings and apparently this admission causes the capillary tube of the burner to dry out and undergo temperature changes between the burnings. A capillary that drys must be washed repeatedly or deposits will form. Intermediate washings, in turn, produce temperature changes strong enough to modify the viscosity and effect the flow rate of the solution being burned. Further, a washing fluid such as acetone when alternated with the not-aqueous solvent may change surface conditions temporarily inside the tiny bore of the aspirating tube. There is at least a strong suspicion that the limitations on precision observed in presently-available equipment is due in part to the use of such open-transfer procedures. Washing, however, may be needed for certain tests samples. If so, one of the test tubes sample holders can be filled with a wash fluid. Alternatively, a wash basin reservoir or tank 45 (FIG. 2) can be provided and this wash fluid can be aspirated into the burner through flexible tubing (not shown) leading to another hypodermic needle, such as needle 39, which can be indexed by the shaft into an aspiratory disposition.

The present valve arrangement essentially is a closed system produced by providing a sealed condition in which essentially no air is admitted during rotation of plate 37 or during burning. To achieve this result, the contacting surfaces of both fixed plate 34 and rotatable plate 37 are flat, highly polished surfaces and, in addition, rotatable plate 37 is tightly held against fixed plate 34 by a heavy spring 41 mounted on the lower portion of shaft 21. Additionally, the mounting of capillary tube 4 in fixed plate 34 utilizes a packing 42 (FIG. 5) held in place by a clamp gland 43 pressured by a spring clamp 44 (FIG. 4). Also, it is preferred to form fixed plate 34 of a dense, tough, plastic material, such as Delrin, and to form rotatable plate 37 of stainless steel having a mating surface which is finely polished with diamond dust. Consequently, no lubricant is needed. Nevertheless, the valve remains airtight and it shows a little wear after extended use.

Several other factors should be noted with regard to the sample changer and its associated valve mechanism. First, as has been indicated, aspirations from the test tubes can be and preferably are made directly from the vessel used in the final separatory phase of the fluid sample preparation. Thus, these test tube holders can be the 100 ml plastic centrifuge tubes which have been described. This procedure, due to the use of plastic dust covers 7 eliminates dust from the air and brings only clean solution to the burner. The preceding centrifuging generally removes the particulates from the organic phase itself. The needles, of course, pierce the covers During loading and, in addition to eliminating dust, etc., the covers retard evaporation. Thus, as long as the samples themselves are carefully prepared and other conditions are stabilized, each of the samples can be burnt in essentially the same flame to produce optical signals providing reliable and extremely precise data. Also, as shown in FIG. 2, the entire sample holding mechanism can be detached from the valve and burner mechanisms by providing a detachable crown-type coupling 50 between the upper end of the shaft and the valve mechanism. The lower end of the shaft can be formed in two detachably-coupled sections which, as desired, also can use a similar crown coupling. Such detachability permits the tests tubes to be mounted on the central clamping section of the shaft and the assembly then to be completed by piercing the valve needles through dust covers 7. Complete detachability of the sample holding central sections permits the preparation of a number of these sections — as united — which then can be quickly substituted one for another much in the manner of cartridge replacements.

Since the sample changer minimizes to the maximum possible degree, the effect of external conditions such as drying, viscosity changes, flame fluctuations, etc., it produces a spectral beam 3 that should be truly representative of the cesium content of the samples. However, it is equally as important to assume that monochromator 8 performs its function in such a manner that the resulting data has the precision and reability needed for the study of cesium or other comparable studies. In this regard, it has been noted that the fact that the cesium spectral peak must be measured while riding on a large spectral continuum requires a wavelength shifting procedure capable of producing a net signal or, in other words, a signal which has the baseline continuum subtracted from it. Generally considered, a feature of the present monochromator is that it utilizes a single exit slit 12 and a single phototube, detector 13 in achieving its purposes. Monochromator having dual slits and requiring dual detectors are known, but their use entails far more elaborate and expensive apparatus and further it imposes the difficult requirement that each of the dual phototube detectors operate in a precisely identical manner. Differences in operating characteristics obviously would downgrade the resulting data.

To permit the use of the single exit slit and a single phototube, a solenoid controlled, pivotal beam-deflecting plate 46 is disposed adjacent to exit slit 12 in the path of reflected beam 3. Mounting of plate 46 can easily be accomplished in any commercial grating monochromator such as the presently-used Czerny-Turner, 1-meter focal length monochromator. Thus, this monochromator has a housing provided in its cover plate which simply can be replaced by a plate which mounts the pivotal mechanism to be described. Functionally considered, plate 46 is pivotal through a fixed angle of 9° although, of course, the arc can be varied to suit conditions. Also, as is known, commercial monochromator employ a grating or equivalent device at their exit slit. The present monochromator, for example, uses a 1200 groove/nm grating. The pivotal movement of plate 46 varies the incidence of the spectral beam on the grating to produce the desired wavelength shift. In the present apparatus, the pivotal movement produces a wavelength shift from 8521 A to 8525 A. As shown, plate 46 shifts the wavelength by refracting the beam. It, however, should be noted that a reflector plate also could be used if, for example, the exit slit were disposed in the top wall of monochromator and the reflector then pivoted to reflect the beam upwardly in the two pivotal directions.

Figures 6, 7, 8:
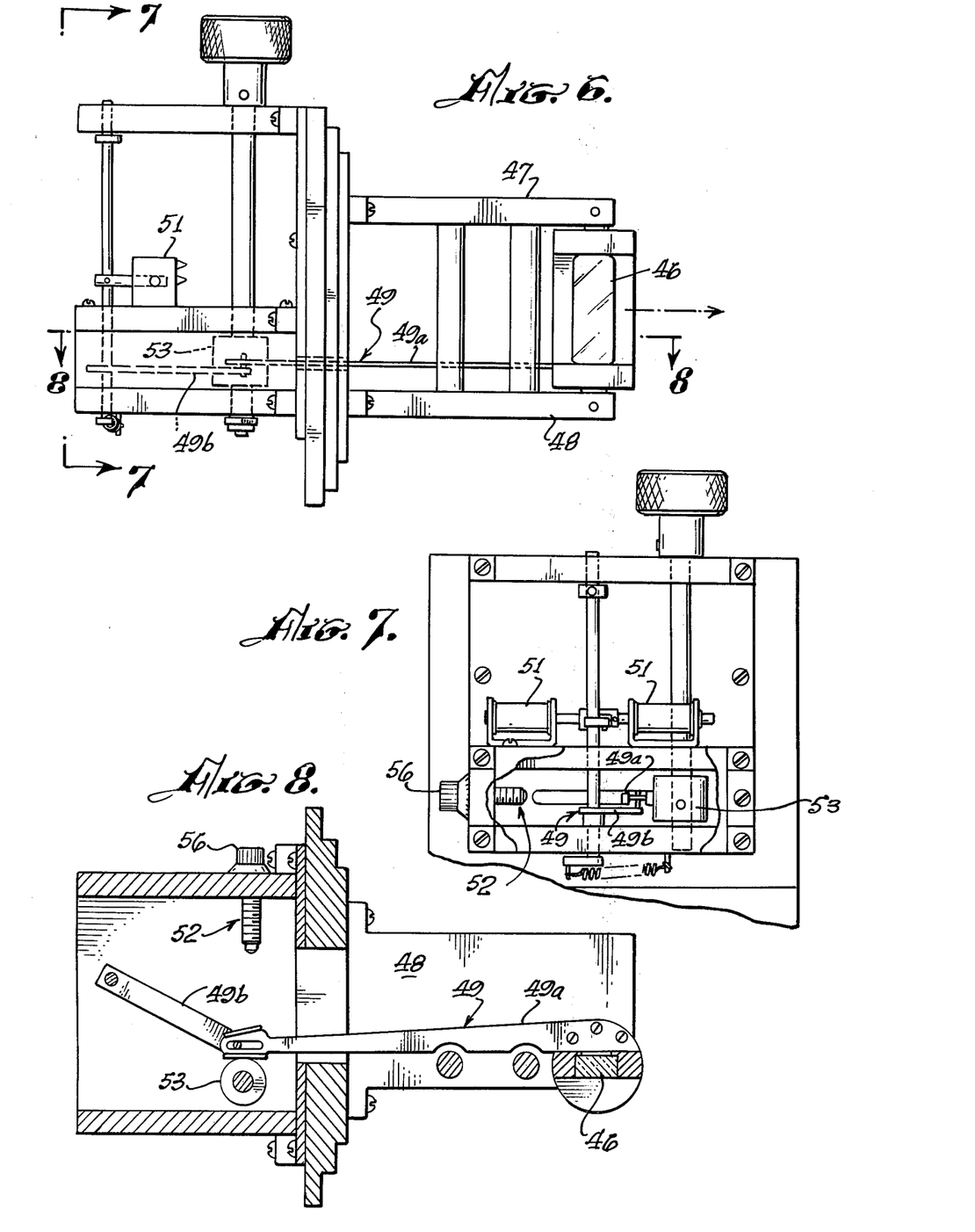
FIG. 6 is a top view illustrating a special wavelength shifting accessory mechanism used in a monochromator of the present system.
FIGS. 7 and 8 are views taken along lines 77 and 88 respectively of FIG. 6.

Details of the wave-shifting mechanism are shown in FIGS. 6–8. Pivotal plate 46, which may be a flat piece of Plexiglas of about ⅝ inch thickness, is mounted on a vertical axis held by preloaded ball bearings which, in turn, are supported by metal plates 47 and 48 which in part replace the cover plate of the monochromator housing. An elongate arm 49 carries plate 46 and produces the pivotal motion. Solenoids 51 and 52 which, as indicated in FIG. 1, are controlled by cycle program 18, which also controls the indexing of the sample changer, are coupled to the rear portion of arm 49 to produce the pivoting motion. More specifically, as shown in FIG. 8, arm 49 is a two-part arrangement having a front portion 49 that carries refractor plate 46 and a rear portion 49b coupled at its end to the solenoids. The two parts, 49a and 49b, are hinged together in the manner shown so that movement of the rear end of portion 49b moves the hinge in a path between two stops 52 and 53 at which points the arm is arrested by the action of a toggle spring arrangement 54.

One of the important factors to be noted, is that, although mechanical stop 53 may be a fixed member, stop 52 utilizes a Vernier adjustment provided by the rotation of a knob 56. As has been noted, the adjustment for baseline wavelengths, such as the 8525 A wavelength of the cesium baseline continuum, are not especially critical since, in effect, the baseline measurements are used to provide a standard for deriving the desired net signal. However, the adjustment for the peak maximum of 8521 A is very critical and, furthermore, this adjustment must be capable of being made quickly and at any time desired by the operator. In the present arrangement the operator is provided with a Vernier mechanism so that, while, for example, a preliminary sample of cesium is being burnt, the operator can rotate this cam stop until he obtains a signal maximum. Subsequently, he may wish to test for possible off-peak drifting using this same adjustment. In operation, a wave shifting mechanism such as that shown in FIGS. 6–8 has demonstrated no significant off-peak drift over a period of several hours and one reason for this stability is the fact that refraction plate 46 is rotated on pairs of preloaded ball bearings held solidly on the mounting plate.

The wave-shifting mechanism permits each sample to be burnt for a short period of time at one of the wavelengths and then, as quickly as possible, to permit the same sample to be burnt for an equal period of time at the other wavelength. In practice, for example, the cesium samples are burnt for a period of 13 seconds at each wavelength with an interval of 0.2 seconds allowed for the shifting of the plate. Again, as will be more fully described, the controls for these functions are provided by cycle program 18.

Plate 46, as has been described, is pivoted between two positions one of which (peak position) can be finely adjusted. However, it may be desirable to provide one or more additional stops (not shown) to permit succession measurements to be taken at several positions. If, as will be appreciated by those familiar with this ar, the continuum, for example, instead of being a horizontal baseline waveform, is slanted upwardly or downwardly, it would be advisable to take measures of the continuum on both sides of the peak waveform. The need for such measurements is a matter that should be recognized by the investigator and, of course, the mechanisms for implementising the additional stops can be readily provided in any desired manner providing that the stop on the peak measurement is adjustable in a highly precise manner.

Figures 9, 10:
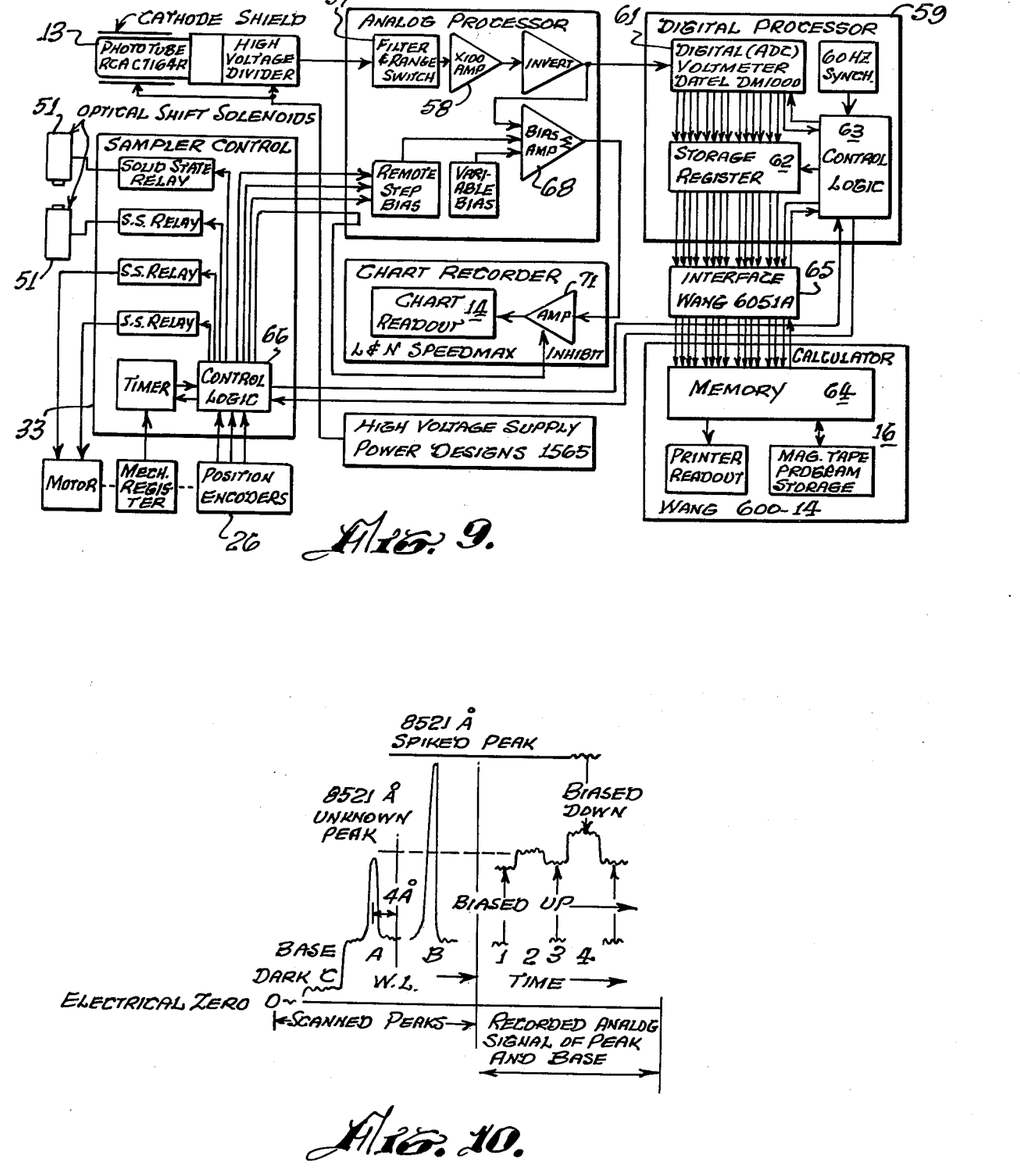
FIG. 9 is a block diagram illustrating in particular a programming system for synchronously commanding the various functions of the system as well as a special biasing arrangement for the chart recorder of the system.
FIG. 10 is a combination view of a pair of recorder traces in which a biased tracing or record of one analysis is compared with an unbiased recording of the same analysis.

The electronics of the system are more fully illustrated in FIG. 9. Generally, simple, modern digital systems is proveded for programming the numerous sampling and data handling operations. Obviously, other functionally-similar arrangements can be substituted. As shown, the electrical signal output of phototube 13 first is passed into an analog processor which contains a filter, a range switch 57 and an amplifier 58. The range switch is used to adjust the signal for widely-varying sample concentrations. In this regard, it has been noted that, although the present system is especially suitable for providing precise measurements of extremely small, microgram concentrations, it also can be used to measure concentrations. Analog processor 57 passes the signal to a digital processor 59 which includes an analog-to-digital converter 61 used to take 350 instantaneous samples which are stored as digital signals in memory 64 of computer 16. A storage register 62 that functions under the command of control logic 63 feeds memory 64. The calculator requires the use of an interface device 65 which may be a commercially-obtainable Wang 6051A unit. As shown, the control logic, derived from block 63, combines with the logic of block 66 to synchronize the calculator with both the position of the sample changer and the position of the wavelength shifter. Thus, control logic 66 is coupled through relays both ot motor 23 which drives the sample changer shaft and to solenoids 51 which control the pivotal motion of wavelength shifting refractor plate 46.

Previously identified, chart recorder 14 is employed for the purpose of providing a visual pen comparison of the signals which are recorded as voltages. However, most standard potentionmetric recorders suitable for flame analyses are not adequate for comparing signals from unknown and spiked reference samples. Their problem is illustrated in FIG. 10. At the left of this figure is represented a cesium spectral peak A derived, for example, from a natural sea water concentrate. Beside spectral peak A is a larger peak B obtained by spiking an aliquot of the same sea water so as to roughly double the amount of cesium naturally present. Considering these peaks, it will be apparent that if, for example, smaller peak A were plotted in the usual manner and with a full-chart amplitude, the large peak B would cause the pen to attemp to run off the chart.

The present system avoids this difficulty by employing a signal biasing technique which assures that the pen is not driven violently off the paper even though, as will be discussed, the signals are higher amplified. Thus, the right-hand side of FIG. 10 illustrates the same signals as the left-hand side except that the right-hand signals have been approximately biased. As shown, the abscissa is time and the four traces represent burnings of an unspiked aliquot at the two wavelengths each followed by a burning of a spiked aliquot at the two wavelengths. All signals, however, are plotted at high gain, biased automatically so as to stay on the chart and, preferably, so that the pen moves very little when changing from one signal to another. Since the baseline signals are much smaller than those of peaks, the baseline signals are biased upwardly while the very large signals from the spiked signals are biased downwardly to levels that permit recording.

Biasing is carried out by algebraically adding a precisely known voltage to the electrical signal coming into the recorder from the photomultiplier tube circuits. These biasing voltages are controlled by the same programmer that controls the rotation of the multiported flat-surfaced valve arrangement as well as the alternations of the wavelengths shifter. Using such arrangement, the performance of the burner of the system can by continuously monitored through inspection of the paper record of the analog pen recorder. Also, by graphically smoothing the pen traces and carefully measuring the average displacements on the chart, concentrations can be derived with acceptable precision providing carefully biasing circuits are employed. On the other hand, the present system contemplates so many individual measurements for each individual sample that a digital computer, such as computer 16 is, in practice, a highly desirable component.

The schematic of FIG. 9 illustrates the biasing principles which have been discussed. As shown, a biasing amplifier 68 is used to add or subtract a precisely-known voltage to the electrical signal derived from the photomultiplier and applied to chart recorder 14. It also should be noted that these biasing voltages are under the control of the control logic of block 66 which also controls the valve rotations and the wavelength shifter. An amplifier 71 applies the signal directly to the recorder and, as shown, the amplifier is inhibited at appropriate times by control logic 66. Obviously, the biasing can be implemented in a variety of manners. However, as far as the present invention is concerned, it should utilize the principles of initial amplification of all inputs following which the added voltages are switched in at levels less subject to switching variabilities and, finally, the analog signal is reduced to levels suitable for the recorder.

Using the present system, actual analytical programs for measuring seawater cesium by flame analysis have been conducted and the programs have shown the extreme sensitivity and precision desired, for example, in the measuring of the unusually small amounts of cesium present in seawater. For example, the precision permits measurements of 0.3 microgram cesium sample with a precision of about 0.3 of a percent. A number of factors contribute to this precision. First, the sample changer utilizes the same test tube holders used in the final step of the sample preparation and the tube contents are protected at all times by dust covers 7 which also prevent evaporation during storage. Hypodermic needles 39 are employed to communicate the samples with the burner and these needles can be pierced through covers 7 during assembly. The flat-faced rotatably-indexed valve plates also contribute significantly in eliminating air from the aspiratory passageways and in minimizing the drying. Thus, each sample is supplied to the burner flame in precisely its prepared condition without being disturbed or affected by external conditions. The resulting flame emission, consequently, permits true comparisons.

The wavelength shifting arrangement of the monochromator is another advantageous factor in that, aside from the advantages inherent in obtaining a net signal, it utilizes the same exit slit and the same photo tube for each wavelength being compared. A single exit slit and a single photo tube not only are relatively simple and unexpensive, they also avoid problems arising because of differing operating characteristics between, for example, dual slits or dual defectors.

The manner in which the apparatus is programmed and used is another highly important factor in improving sensitivity and precision. Thus, the system is capable of using modern digital techniques which obtain a multiplicity (350) of instantaneous samples for each burning permits an integration of these samples to provide a highly reliable average and deviation for each burning. If, as is contemplated, each sample is burned for 13 seconds at each wavelength (peak and baseline) each of these burning provides the 350 digital samples for integration in the computer. The time required to produce the wavelength shaft is only about 0.2 of a second. Further, the sample changer arrangements not only permits indexing of each sample, it further permits each sample to be burned repetitively or a plural number of times. As presently used, the four samples each are burned at the different wavelengths for 13 seconds and, in addition, each of the samples is burned six or nine times. The rotary motion of the valve mechanism permits the repetitive burnings. Each burning, in turn, is stored in the computer memory which then is programmed into the computer to be compared in the other five burnings and the integrating comparison is made between the multiplicity of instantaneous signals. The use of the programmed computer is a significant contribution. Also, the use of digital logic to control and synchronize the operations of the sample changer, the wavelength shifter and the computer insures precise actions with precise time sequences. The chart records also provide a visual record of the flame-emission signals although the record obviously does not have the sensitivity of the integrated computer record. Even so, the recorder record is most helpful in that it provides a visual method of adjusting the apparatus for maximum sensitivity. For example, the chart recorder can be used by the operator to finely adjust the wavelength changer to achieve an absolute peak intensity.

In general, the success of the system which has demonstrated an inherent reproducability of less than ⅓ percent is due to the use of the true mechanical eliments, ie, the sample changer and wavelength shifter, in a manner which permits whem to perform reliable, under control of an automatic programmer.

Obviously many modifications and variations of the present invention are possible in the light of the above teachings. It is, therefore, to be understood that within the scope of the appended claims the invention may be practiced otherwise than as specifically described.

We claim:

1. Apparatus for use with a flame-emission spectrometer having an aspirator tube feeding a liquid test sample to a burner flame for producing photoelectrically-detectable spectral line emission beams, said apparatus comprising:
    a fixed valve plate having a port sealably receiving said aspirator tube,
    a movably-indexable valve plate provided with a plurality of capillary-sized ports disposed for communication with said fixed plate port when said movable plate is indexed,
    an elongate hollow-bore aspirating tube mounted in and dependently carried by each of said movable plate ports,
    a plurality of liquid sample holders each disposed for immersibly receiving one of said elongate tubes,
    drivable support means carrying said indexable valve plate and said sample holders, and
    means for driving said support means for successively indexing said movable plate and holders into aligned communication with said fixed plate port whereby each fluid sample can be aspirated into said burner flame,
    said fixed and movable valve plates having mating flat valve-face surfaces constantly maintained in flush contact one with the other for excluding atmospheric leakage into said ports.

2. The apparatus of claim 1 wherein said movable valve plate is rotatably driven and said plurality of capillary-sized ports are arcuately spaced one from another in a circular path whereby each port can be rotatably indexed in a repetitious manner into communication with said afixed valve plate port.

3. The apparatus of claim 2 wherein said support means is a drive shaft,
    said apparatus further including means carried by said shaft for resiliently urging said rotatable parts into said contact with the fixed plate.

4. The apparatus of claim 3 wherein said fixed valve plate is formed of a tough dense plastic material and the mating surface of said rotatable valve plate is formed of a highly polished metal.

5. The apparatus of claim 3 further including:
    digital logic means for controlling said rotary indexing movements, and
    optical indicator means including circuit means coupled to said logic means for triggering said logic means when said plate ports are in said aligned communication.

6. The apparatus of claim 5 wherein said optical indicator means includes:
    an apertured plate rotatably carried by said drive shaft and provided with a plurality of apertures disposed in accordance with said rotatable valve plate ports, and
    an optical beam transceiver straddling said apertured plate in position for transmitting the beam through said apertures,
    said triggering circuit means including said optical beam whereby said logic means is triggered when said apertures permit transmission of said optical beam and said aperture disposition being such that said transmission is permitted only when said valve ports are in said aligned communication.

7. The apparatus of claim 1 wherein said elongate aspirating tubes are sharply pointed hypodermic-type needles and wherein said sample holders further include:
    membrane-like cover sheets sealably enclosing said test samples whereby said covers can be pierced by said needles when said sample holders are mounted on said holder-carrying-drivable support means.

8. The apparatus of claim 1 wherein said flame-emission spectrometer is of a type having a monochromator adapted to receive a flame-emitted spectral beam and to direct said received beam in an optical path to an exit slit, said apparatus further including:
    a single phototube means optically communicated with said exit slit for receiving said beam and producing a corresponding electric signal output and a beam-deflecting plate pivotally mounted in said monochromator adjacent to said exit slit in the optical path of said beam,
    said plate being pivotal between at least two positions for shifting the beam a predetermined amount whereby the impinging direction of the beam on said exit slit can be varied to induce a wavelength shift in the beam received by said phototube.

9. The apparatus of claim 8 further including:
    venier-like means for adjusting at least one of said positions, said means projecting outwardly of said monochromator for permitting manual adjustments.

10. The apparatus of claim 9 further including: chart recorder means operatively coupled to the output of said phototube for producing a visual trace of said signal output, whereby said manual adjustments can be manually regulated by said visual trace.

11. The apparatus of claim 10 further including means for biasing said recorder trace, said biasing means comprising:
    means for amplifying said phototube output signal, and
    means for algebraically adding a known voltage to said amplified output for regulating the magnitude of said trace in accordance with the available size of the chart recorder record sheet,
    said voltage being subtracted from said amplified output when the test sample concentration is high and being added to said amplified output when said concentration is low, and
    means synchronized with said sample holding indexing movements for coordinating said addition and subtraction with the particular test sample being burned.

12. The apparatus of claim 8 further including:
    electrically-energizable means for pivotally moving said beam deflector plate between said positions, and
    digital logic means operatively coupled ot said energizable means and to said means for indexable driving said sample holder support means for synchronizing the pivotal movements with the particular test sample being burned.

13. The apparatus of claim 12 further including:
    analogue processing means coupled to said phototube output signal for converting the signal produced by each burn into a multiplicity instantaneous digital signals, digital computing means having a memory component receiving said multiplicity of instantaneous digital signals for each burn, said digital logic means also controlling said computer for coordinating its operation with the particular test sample being burned and with the pivotal movements of said beam-deflecting plate.

14. The apparatus of claim 13 wherein said port arrangements of said movable valve plate permits said communication of each port with the port of said fixed plate to be repetitively established whereby plural unknown and standard test samples each can be repetitively burned at selected wavelengths for producing a repetitive digital output for each burning, said digital logic means being programmed to cause said computer to integrate said multiplicity of instantaneous signals and to compute an average concentration and a standard deviation based upon said repetitive signal data.

15. The apparatus of claim 14 wherein the precision of said computations, as established by known test sample burnings, is in the order of a few tenths of one percent.

* * * * *